United States Patent [19]

Chaung

[11] Patent Number: 5,082,977
[45] Date of Patent: Jan. 21, 1992

[54] ALDEHYDES BY OLEFIN HYDROFORMYLATION

[75] Inventor: Steven S. C. Chaung, Akron, Ohio

[73] Assignee: University of Akron, Akron, Ohio

[21] Appl. No.: 649,377

[22] Filed: Jan. 31, 1991

Related U.S. Application Data

[63] Continuation of Ser. No. 480,642, Feb. 15, 1990, abandoned.

[51] Int. Cl.$^5$ ............................................. C07C 45/50
[52] U.S. Cl. ................................. 568/454; 568/451; 568/452
[58] Field of Search ........................ 568/451, 452, 454

[56] References Cited

U.S. PATENT DOCUMENTS

| | | | |
|---|---|---|---|
| 2,558,508 | 6/1951 | Appleby et al. | 502/222 |
| 2,559,325 | 7/1951 | Spillane | 502/222 |
| 2,559,325 | 7/1951 | Spillane | 502/222 |
| 2,822,397 | 2/1958 | Winstrom | 502/222 |
| 3,223,652 | 12/1965 | Erickson | 502/222 |
| 3,487,112 | 12/1969 | Paulik | 260/604 |
| 3,994,978 | 11/1976 | Whitehurst | 568/451 |
| 4,210,608 | 7/1980 | Pinke | 568/451 |
| 4,213,921 | 7/1980 | Mitchell et al. | 568/455 |
| 4,222,966 | 9/1980 | Bexten et al. | 568/451 |
| 4,361,711 | 11/1982 | Blaskie et al. | 568/909 |
| 4,506,101 | 3/1985 | Chang | 568/454 |
| 4,536,492 | 8/1985 | Haines | 502/222 |
| 4,590,314 | 5/1986 | Kinkade | 568/451 |

FOREIGN PATENT DOCUMENTS

| | | | |
|---|---|---|---|
| 0149256 | 7/1985 | European Pat. Off. | |
| 2453229 | 5/1976 | Fed. Rep. of Germany | 568/451 |

OTHER PUBLICATIONS

"Use of Sulfur-Containing Oils for Production of Higher Alcohols by Oxosynthesis", by Freund & Markó.

Primary Examiner—Werren B. Lone
Attorney, Agent, or Firm—Oldham & Oldham Company

[57] ABSTRACT

Olefins are reacted with carbon monoxide and hydrogen to produce aldehydes to the near exclusion of alcohols in the presence of a solid phase catalyst consisting essentially of one or more sulfided Group VIII metals.

18 Claims, No Drawings

ALDEHYDES BY OLEFIN HYDROFORMYLATION

This is a divisional of copending application Ser. No. 07/480,642 filed on Feb. 15, 1990, abandoned.

FIELD OF THE INVENTION

The present invention relates to the production of aldehydes by the hydroformylation of olefins in the presence of a solid phase heterogeneous catalyst. More specifically, the present invention relates to a process for producing aldehydes having at least three carbon atoms from olefins having at least two carbon atoms in the presence of carbon monoxide and hydrogen and a solid phase heterogeneous catalyst. Even more specifically, the present invention relates to a process for producing said aldehydes from olefins utilizing a catalyst consisting essentially of one or more sulfided metal of Group VIII. Still more specifically, the present invention relates to a process for producing the aldehydes from olefins in the presence of carbon monoxide and hydrogen and a solid phase heterogeneous catalyst with a very high selectivity to the aldehyde rather than the related alcohol.

BACKGROUND OF THE INVENTION

The production of aldehydes and alcohols by the reaction of olefins with carbon monoxide and hydrogen is well known and well described in many U.S. patents, including U.S. Pat. No. 2,880,241, to Hughes. The general reaction for the preparation of aldehydes is:

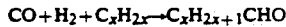
$$CO + H_2 + C_xH_{2x} \rightarrow C_xH_{2x+1}CHO \qquad (I)$$

From this point, the aldehyde produced in Reaction I may be hydrogenated to produce an alcohol by the reaction

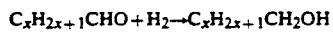
$$C_xH_{2x+1}CHO + H_2 \rightarrow C_xH_{2x+1}CH_2OH \qquad (II)$$

This second reaction is not always desired, and, in some particular instances, the preferred product is the aldehyde rather than the alcohol. The catalytic process of the present invention discloses one method of obtaining the aldehyde product almost to the exclusion of the alcohol. As the catalyst of the present invention is a heterogeneous catalyst that can be easily separated from the products of the reaction, further treatment of the products, particularly the aldehydes, may be accomplished in a separate reactor, with or without a catalyst, to obtain other reaction products of the aldehydes, including the alcohols, if so desired. The persons skilled in the chemical arts will be already in possession of the knowledge of how to react aldehydes to other useful chemical species.

The carbon monoxide and hydrogen mixture required to react with the olefin or olefins would be readily and economically available if the synthesis gas, which is a generic term for a variety of mixtures of carbon monoxide and hydrogen, produced by conventional coal gasification processes was free from sulfur contaminants, particularly hydrogen sulfide. Sulfur compounds, however, are known to be poisons of the catalysts known in the prior art, so costly desulfurization processes are required in the preparation of a synthesis gas for the desired reaction. For example, see Carberry, Chemical and Catalytic Reaction Engineering, McGraw-Hill, 1976, at 396.

Further, as recognized and noted by Blaskie, et al., in U.S. Pat. No. 4,361,711, the prior art has, in general, been conducted in the liquid phase, using various solvents for controlling concentration of soluble reactants, reactants and catalysts which are present in a homogeneous single phase system. Because the reactants, products, and catalysts are present in the same phase, this type of hydroformylation reaction requires a separation step, after the actual hydroformylation stage, to recover the catalyst from the product stream. Catalyst recovery and regeneration has been one of the major costs and investments in commercializing these liquid phase processes. These costs are especially pernicious when the catalysts contain rare metals.

It should be noted that many of the known effective catalysts used in the liquid phase processes are the metal carbonyls and their modified forms. This type of homogeneously catalyzed reaction is often referred to as the "Oxo" process.

In attempts to avoid the expensive separation steps after hydroformylation for homogeneous phase catalysts and to minimize the costs of catalyst losses in the product, various researchers have used polymers or oxides as anchoring agents for metal complex catalysts as well as use of mixed metal oxides as catalysts. Although a heterogeneous phase catalyst can be achieved, these catalysts still suffer from sulfur poisoning, and they have additional problems of poor activity, selectivity, and thermal stability. Ideally, an excellent hydroformylation catalyst should be active and selective to a desired product, i.e., aldehyde; be resistant to sulfur poisoning; and be a solid phase catalyst to minimize purification of the products and catalyst loss in the product.

SUMMARY OF THE INVENTION

A first object of the present invention is to produce aldehydes by the reaction of olefins with carbon monoxide and hydrogen.

A second object of the present invention is to prepare aldehydes to the near exclusion of alcohols, that is, to produce aldehydes with a catalyst that has a very selectivity to aldehyde as compared to the selectivity to alcohol.

A third object of the present invention is to produce aldehydes by the reaction of olefins with carbon monoxide and hydrogen in a process that is not vulnerable to poisoning by sulfur-containing species in the feedstock.

A fourth object of the present invention is produce aldehydes by the reaction of olefins with carbon monoxide and hydrogen by use of a heterogeneous solid phase catalyst that obviates costly separation processes currently required to recover the conventional homogeneous catalysts.

These and still further objects of the present invention are achieved by a process for producing aldehydes containing at least three to carbon atoms by the reaction of an olefin or a mixture of olefins, said olefin or mixture thereof having at least two carbon atoms, with carbon monoxide and hydrogen over a solid phase catalyst.

The process is carried out in the temperature range of 70°–350° C. and a pressure range of 1–100 atmospheres, at gas hour space velocities in the range of 10 to 100,000 $hr^{-1}$. The feedstock may contain sulfur, particularly $H_2S$ or $CS_2$, without deleteriously affecting catalyst performance.

The catalyst is essentially of the formula $A_xMS_yMn_z$, where A is an alkali metal; M is a Group VIII metal; S is sulfur; Mn is manganese; x and z are in the range of 0 to 10; and y is in the range from 0.01 to 2. The preferred Group VIII metals are nickel, cobalt, iron and rhodium.

The catalyst is preferably used with a support material to increase the active surface area. The support material may be selected from supports commonly known in the art.

DETAILED DESCRIPTION OF THE PREFERRED EMBODIMENT

Reactants

The reactants for the present invention are an olefin or mixture of olefins, carbon monoxide and hydrogen. The preferred olefins have six or fewer carbon atoms and the most preferred are either ethylene or propylene, although the catalyst is effective with olefins containing more than two carbon atoms.

The feedstock for the reactor may contain sulfur compounds, particularly hydrogen sulfide and carbon disulfide, in the range of up to 20,000 ppm.

The molar ratio of reactants in the feedstock is not critical to the operation of the process, provided that all three reactants are present. It will be readily appreciated that increasing carbon monoxide and olefin concentrations with respect to hydrogen will usually increase selectivity toward the aldehyde product rather than the paraffin and alcohol. This is due to the role of hydrogen in Reaction II set forth above. It will also be readily apparent that the stoichiometry of the reactions will prefer a 1:1:1 molar ratio of $CO:H_2:Olefin$ to increase selectivity towards aldehyde and a 1:2:1 molar ratio to increase selectivity towards alcohol.

Process Conditions

The process of the present invention may be conducted under temperature conditions ranging from about 70° to about 350° C. The preferred range is from about 130° to about 250° C.

The process of the present invention may be conducted at pressures from about 1 to about 100 atmospheres, with the preferred pressure being in the range of about 10 to about 30 atmospheres.

The reaction may be conducted at gas hour space velocities (GHSV), that is, volumes of reactant gas per volume of the reactor per hour, expressed usually in reciprocal hours, in the range of from 10 to 100,000 $hr^{-1}$.

Catalyst

The catalyst of the present invention essentially comprises four components: at least one metal chosen from the Group VIII metals, that is, the group comprising iron, cobalt, nickel, ruthenium, rhodium, palladium, osmium, iridium and platinum; sulfur; at least one alkali metal, that is, at least one metal from the group comprising lithium, sodium, potassium, rubidium, cesium and francium; and manganese. The composition of the catalyst may be expressed as $A_xMS_yMn_z$, where A is the alkali metal or mixture of alkali metals; M is the Group VIII metal or mixture of Group VIII metals; S is sulfur; Mn is manganese; x and z are in the range of 0 to 10; and y is in the range from 0.01 to 2. If present, the alkali metal and the manganese can be in the form of oxide, carbonate, sulfide, or some combination thereof.

The catalyst can be used with or without a catalyst support that is conventionally known for supporting the catalyst on a support surface to increase active surface area, although it is preferred to use such support. Typical oxide supports are $SiO_2$, $Al_2O_3$, $TiO_2$, ZnO, MgO, $La_2O_3$, MnO and $ZrO_2$, although it will be obvious to one of skill in the art of catalyst preparation that this listing is for illustrative purposes only and certainly not intended to limit the scope of the supports available.

A few methods of preparing the catalyst of the present invention are presented herewith.

A. Impregnation Method

A first method of preparing the catalyst of the present invention is by impregnation of the selected catalyst support material, a technique which will be generally familiar to one of skill in the catalyst art.

Oxide-supported catalysts of the present invention can be prepared by impregnating the oxide support material with Group VIII metal precursors, such as Group VIII metal nitrates, chlorides, carbonyls, and complexes. These precursors may be either water- or organic soluble, depending upon the selected solvent. Typical solvents would be water, methanol, ethanol, acetone, and pentane.

The impregnation solution is prepared by dissolving the selected Group VIII metal precursors in a volume of the selected solvent that is approximately equal to the total pore volume of oxide support material to be impregnated. The impregnation solution is then added slowly to the oxide support material.

Following the impregnation, the catalyst is dried by conventional means at 20°-60° C. Once dried, the catalyst can be either calcined to form oxides by heating at 150°-400° C. or reduced to metal by heating at 220°-500° C.

The alkali or manganese component, or both, can be added to the catalyst by either sequential impregnation or co-impregnation using soluble precursors as described above for the Group VIII metal, followed by the same drying and calcining or reducing procedure described above.

Once impregnated with Group VIII metal and alkali, manganese, or both alkali and manganese, and calcined or reduced, the resulting material is sulfided by a gas containing a sulfur compound such as hydrogen sulfide in hydrogen When hydrogen sulfide is used, the sulfiding gas can range from about 10 ppm $H_2S$ in $H_2$ to pure $H_2S$. The sulfidation is carried out in the temperature range of 200°-500° C. From the experiments conducted by the inventor in preparing the catalysts, it appears that catalyst activity and selectivity are independent of sulfidation temperature, at least within the range cited.

B. Co-precipitation Method

A second method of preparing the catalyst of the present invention is by the co-precipitation method, again a method generally known to one skilled in the catalyst art. As will be appreciated from this described procedure, catalysts prepared in this manner are unsupported.

The selected water-soluble Group VIII metal or metals, alkali or alkalis and manganese compounds, which are usually in the form of nitrates or chlorides, are dissolved in an aqueous solution. Then alkali carbonate or hydroxide is used as precipitating agent to form carbonate precipitates of the Group VIII metal or metals and the manganese, all of which are almost insoluble in water. It will be appreciated that some alkali concentration will be captured in the resulting precipitate as it forms. Excess alkali, if any, can be washed off of the precipitate by using warm water.

Following the co-precipitation step, the precipitate is dried by conventional means at 20°-60° C. Once dried, the catalyst can be either calcined to form oxides by heating at 150°-400° C. or reduced to metal by heating in a reducing atmosphere, preferably one with a high concentration of hydrogen, at 220°-500° C.

Once dried and calcined or reduced, the resulting material is sulfided by a gas containing a sulfur compound such as hydrogen sulfide in hydrogen. When hydrogen sulfide is used, the sulfiding gas can range from about 10 ppm $H_2S$ in $H_2$ to pure $H_2S$. The sulfidation is carried out in the temperature range of 200°-500° C. From the experiments conducted by the inventor in preparing the catalysts, it appears that catalyst activity and selectivity are independent of sulfidation temperature, at least within the range cited.

C. Direct Precipitation of Group VIII metal sulfide

A third method of preparing a catalyst of the present invention is by direct precipitation of the sulfides of the selected Group VIII metal or metals, and manganese, if desired. As with the co-precipitation method described above, the resulting catalyst will be unsupported.

Group VIII metal sulfide can be prepared by addition of aqueous solution of alkali sulfide to an aqueous solution of a water-soluble Group VIII metal salt, preferably chloride or nitrate, resulting in the formation of a Group VIII metal sulfide precipitate at room temperature. If manganese is desired in the catalyst, the aqueous solution should contain an appropriate amount of a water-soluble manganese salt, again preferably manganese chloride or nitrate. This material is dried by conventional means at 20°-60° C.

D. Other Preparation Methods

Although three specific methods of preparing the catalyst of the present invention are presented, they are not to be considered as limiting the possible methods of preparing the catalyst, but merely as illustrative of the techniques available to the person of ordinary skill in the catalyst art.

E. Means of Supporting the Catalyst

It will also be appreciated by those of skill in the catalyst art that this composition can be formed into any desirable type of shape for use in a fixed-bed type of reactor, including, for illustrative purposes: tubes, spheres, INTALOX TM saddles, SUPER INTALOX TM saddles, Berl saddles, MINIRING TOWER PACKING TM, RASCHIG RINGS TM, cross-partition rings, Lessing rings, Pall rings, Tellerettes and pellets. It can also be prepared in a size range and distribution suitable for fluidization.

EXAMPLES

Example 1

Ten (10) grams of a large pore silica having a surface area of approximately 350 square meters per gram was impregnated with 12 ml of an aqueous solution containing 7.4 grams of $Ni(NO_3)_2$ hexahydrate by using the impregnation method described above, followed by drying and sulfiding procedures also described. The resulting catalyst contained ten (10) weight percent of Ni. The molar ratio of S to Ni, determined by energy-dispersive spectroscopy, was 0.42.

Approximately 0.3 grams of the catalyst so prepared was packed in a stainless steel tube with an outside diameter of ⅜". The packed tube was operated as a differential reactor. A mixture of synthesis gas and ethylene having a molar ratio $CO:H_2:C_2H_4$ of 1:1:1 was passed through the packed tube at a gas hour space velocity (GHSV) of 1200 $hr^{-1}$ and a pressure of 10 atm. Adding 1000 ppm $H_2S$ to the feedstock was found to have no effect on the rate of reaction and product distribution. The reactor was maintained at a constant temperature in the range of 90° to 300° C. during each run, although the temperature was varied from run to run.

The reactor effluent was injected to a gas chromatograph using a 6 ft. PORAPAK PS TM column in series with 6 ft. PORAPAK QS TM column. This combination of two columns was found to permit a good on-line separation of all hydrocarbons in the one- to seven-carbon atom range, particularly the aldehydes and alcohols. The reaction results, including rates of ethylene conversion and product distribution are listed in Table 1.

Example 1A

A catalyst was prepared in the same manner as in Example 1 except that 12 ml of aqueous solution containing 2.5 grams of $Co(NO_3)_2$ hexahydrate was used. The resulting catalyst contained 5 weight percent of Co. The molar S:Co ratio, as determined by energy-dispersive spectroscopy, was 0.3.

When approximately 0.3 grams of the catalyst was packed in a stainless steel tube identical to that used in Example 1, the reaction conditions of Example 1 were duplicated, and the effluent identically analyzed, the results as listed in Table I were obtained.

Example 1B

A catalyst was prepared in the same manner as in Example 1 except that 12 ml of aqueous solution containing 4.9 grams of $FeCl_3$ hexahydrate was used. The resulting catalyst contained 10 weight percent Fe. The molar ratio of S to Fe was determined to be 0.2.

When approximately 0.3 grams of the catalyst was packed in a stainless steel tube identical to that used in Example 1, the reaction conditions of Example 1 were duplicated, and the effluent identically analyzed, the results as listed in Table I were obtained.

Example 1C

A catalyst was prepared in the same manner as in Example 1 except that 11 ml of an aqueous solution containing 0.82 grams of $H_2OsCl_6$ hexahydrate was used. The resulting catalyst contained 3 wt. % Os. The molar ratio of S to Os was determined to be 0.11.

When approximately 0.3 grams of the catalyst was packed in a stainless steel tube identical to that used in Example 1, the reaction conditions of Example 1 were duplicated, and the effluent identically analyzed, the results as listed in Table I were obtained.

Example 1D

A catalyst was prepared in the same manner as in Example 1 except that 10 ml of aqueous solution containing 0.55 grams $IrCl_3$ trihydrate was used. The resulting catalyst contained 3 wt. % Ir. The molar ratio of S to Ir was determined to be 0.12.

When approximately 0.3 grams of the catalyst was packed in a stainless steel tube identical to that used in Example 1, the reaction conditions of Example 1 were duplicated, and the effluent identically analyzed, the results as listed in Table I were obtained.

Example 1E

A catalyst was prepared in the same manner as in Example 1 except that 10 ml of aqueous solution containing 0.7 grams of a hydrated $RuCl_3$ comprising 43 wt. % water was used. The resulting catalyst contained 3 wt. % Ru. The molar ratio of S to Ru was determined to be 0.12.

When approximately 0.3 grams of the catalyst was packed in a stainless steel tube identical to that used in Example 1, the reaction conditions of Example were duplicated, and the effluent identically analyzed, the results as listed in Table I were obtained.

Example 1F

A catalyst was prepared in the same manner as in Example 1 except that 12 ml of aqueous solution containing 0.87 grams of $Rh(NO_3)_3$ and 0.28 grams of $CsNO_3$ were used. The resulting catalyst contained 3 wt. % Rh. The molar ratio of S:Cs:Rh was determined to be 0.14:0.5:1.

When approximately 0.3 grams of the catalyst was packed in a stainless steel tube identical to that used in Example 1, the reaction conditions of Example 1 were duplicated, and the effluent identically analyzed, the results as listed in Table I were obtained.

Example 2

A catalyst containing sulfur, nickel, manganese, and sodium was prepared by the co-precipitation method described more fully above. A first solution was prepared by adding 12 grams of $Mn(NO_3)_3$ trihydrate and 29 grams of $Ni(NO_3)_2$ hexahydrate to a beaker and adding water until a total solution volume of 400 ml was achieved. A second aqueous solution containing 20 grams of $Na_2CO_3$ in 200 ml of total solution was prepared and added to the first solution, resulting in the formation of carbonate precipitates of the Ni and Mn.

After drying and sulfidation in the manner described above, the resulting catalyst was determined to have a molar ratio of Na:Mn:Ni of 0.005:0.5:1. There was no determination of the sulfidation level of this catalyst.

A reaction study was performed on the catalyst in the same manner as described in Example 1. Results obtained are presented in Table I.

Example 3

A 100 ml aqueous solution containing 4.6 grams of $Li_2S$ was added to a 200 ml aqueous solution containing 29 grams of $Ni(NO_3)_2$ hexahydrate to precipitate black NiS. The resulting precipitate was washed with warm water and dried at room temperature.

A reaction study was performed on the catalyst in the same manner as described in Example 1. Results are presented in Table I.

Example 3A

The catalyst prepared in Example 3 was also tested for propylene hydroformylation. The reaction was conducted in the same manner as in Example 1 except that propylene was used instead of ethylene. The reaction temperature was 272° C.

The product composition was determined to be:

| | |
|---|---|
| methane | 2 mole % |
| ethane | 3 mole % |
| n-propane | 73 mole % |
| n-butyraldehyde | 14 mole % |
| i-butyraldehyde | 8 mole % |

The rate of propylene conversion is 0.21 mole/kg-hr.

In Table 1 presented herewith, the conversion rates of ethylene ($C_2H_4$) are presented in moles per kg-hr. The selectivities of ethylene to the various products (methane, ethane and acetaldehyde) are presented as mole percentages, and were calculated by determining the ratio of the rate of formation of the specific product to the rate of conversion of ethylene. All examples have their selectivity data rounded to the nearest 1 percent. As no example presented herein yielded ethanol in any amount that would round to other than 0%, no data are presented for ethanol in Table 1. In each and every case, the selectivity of the catalyst to the aldehyde species is at least ten times the selectivity of the catalyst to the corresponding alcohol species.

All of the data in Table 1 were collected at a reactor pressure of 10 atmospheres.

While the examples presented herewith illustrate the use of a single Group VIII metal and a single alkali, it is clear that the present specification puts the preparation and testing of embodiments containing more than one Group VIII metal, more than one alkali, or both, well within the skill of one of ordinary skill in this art. Further, while the examples presented do not illustrate the use of each and every Group VIII metal or alkali metal, the known properties of these materials may be used to anticipate the effectiveness of a particular catalyst that may be produced by the methods taught herein. It is clear from the data presented that the most preferred catalysts disclosed herein are those that utilize the Group VIII metals in the "upper right" corner of the group as customarily presented in a periodic table of the elements, that is, nickel, cobalt, rhodium and palladium.

While in accordance with the patent statutes a preferred embodiment and best mode have been presented, the scope of the invention is not limited thereto, but is to be measured by the scope of the attached claims.

TABLE 1

| Example | Temp. (°C.) | Conversion (mole %) | Conv. Rate (mole/kg-hr) | Selectivities (mole %) | | |
|---|---|---|---|---|---|---|
| | | | | $CH_4$ | $C_2H_6$ | $C_2H_5CHO$ |
| 1 | 240 | 13.5 | 20.1 | 1 | 32 | 67 |
| 1 | 275 | 17.6 | 26.2 | 0 | 60 | 40 |
| 1 | 300 | 18.4 | 27.4 | 0 | 70 | 30 |
| 1A | 240 | 5.6 | 8.3 | 0 | 81 | 19 |
| 1A | 210 | 2.7 | 4.0 | 0 | 73 | 27 |
| 1B | 300 | 0.27 | 0.4 | 14 | 78 | 8 |
| 1B | 240 | 0.05 | 0.08 | 40 | 16 | 44 |
| 1C | 270 | 0.74 | 1.1 | 0 | 94 | 6 |
| 1D | 270 | 6.7 | 10.0 | 2 | 88 | 10 |
| 1E | 210 | 0.1 | 0.15 | 10 | 64 | 26 |
| 1F | 300 | 0.14 | 0.20 | 1 | 30 | 69 |
| 2 | 300 | 1.0 | 1.5 | 1 | 28 | 71 |
| 3 | 150 | 0.006 | 0.008 | 45 | 35 | 20 |
| 3 | 180 | 0.009 | 0.013 | 60 | 18 | 22 |
| 3 | 210 | 0.017 | 0.025 | 48 | 12 | 40 |
| 3 | 240 | 0.04 | 0.06 | 12 | 3 | 85 |
| 3 | 275 | 0.07 | 0.07 | 8 | 4 | 88 |

I claim:

1. A process for producing aldehydes having at least three carbon atoms and less than eight carbon atoms, by the reaction of an olefin or a mixture of olefins, said olefin or mixture thereof having at least two carbon atoms and less than seven carbon atoms, with carbon monoxide and hydrogen over a solid phase catalyst, at a temperature from about 70° C. to about 350° C. and at a pressure from about 1 to about 100 atmospheres, said catalyst being essentially of the formula:

$$A_xMS_yMn_z$$

where
A is an alkali metal or mixture of alkali metals;
M is a Group VIII metal or mixture of Group VIII metals;
S is sulfur;
Mn is manganese;
x and z are in the range of 0 to 10; and
y is in the range from 0.01 to 2.

2. The process of claim 1 wherein the solid phase catalyst is supported on a catalyst support.

3. The process of claim 2 wherein the catalyst support is selected from the group of metal oxides comprised of $SiO_2$, $Al_2O_3$, $TiO_2$, ZnO, MgO, $La_2O_3$, MnO and $ZrO_2$.

4. The process of claim 1 wherein the reaction is conducted in the presence of sulfur-containing species in the range of 0 to 20,000 ppm without deleterious effect on the catalyst.

5. The process of claim 4 wherein the sulfur-containing species is hydrogen sulfide.

6. The process of claim 1 wherein at least one of the Group VIII metals is nickel.

7. The process of claim 1 wherein at least one of the Group VIII metals in the catalyst is cobalt.

8. The process of claim 1 wherein at least one of the Group VIII metals in the catalyst is iron.

9. The process of claim 1 wherein at least one of the olefins reacted is ethylene.

10. The process of claim 1 wherein at least one of the olefins reacted is propylene.

11. The process of claim 1 wherein the reaction temperature is in the range of about 70° to about 350° C.

12. The process of claim 11 wherein the reaction temperature is in the range of about 130° to about 250° C.

13. The process of claim 1 wherein the reaction pressure is in the range of about 1 atmosphere to about 100 atmospheres.

14. The process of claim 13 wherein the reaction pressure is in the range of about 10 atmospheres to about 30 atmospheres.

15. The process of claim 1 wherein all reactants and products are in the vapor phase and the catalyst is in the solid phase.

16. The process of claim 1 wherein the relative selectivity of the catalyst for aldehyde to alcohol is at least 10:1.

17. The process of claim 1 wherein the temperature is from about 130° C. to about 250° C.

18. The process of claim 1 wherein the pressure is from about 10 atmospheres to about 30 atmospheres.

* * * * *

UNITED STATES PATENT AND TRADEMARK OFFICE
CERTIFICATE OF CORRECTION

PATENT NO. : 5,082,977
DATED : 01/21/92
INVENTOR(S) : Steven S.C. Chaung

It is certified that error appears in the above—identified patent and that said Letters Patent is hereby corrected as shown below:

Title page, item (19) and (75) should read-- Steve S.C. Chuang--.

Signed and Sealed this

Thirteenth Day of April, 1993

*Attest:*

STEPHEN G. KUNIN

*Attesting Officer*     *Acting Commissioner of Patents and Trademarks*